US007806885B2

(12) United States Patent
Inoue et al.

(10) Patent No.: US 7,806,885 B2
(45) Date of Patent: Oct. 5, 2010

(54) DISPOSABLE DIAPER

(75) Inventors: Toshio Inoue, Kagawa-ken (JP); Satoru Tange, Kagawa-ken (JP)

(73) Assignee: Uni-Charm Corporation, Ehime (JP)

(*) Notice: Subject to any disclaimer, the term of this patent is extended or adjusted under 35 U.S.C. 154(b) by 174 days.

(21) Appl. No.: 11/626,463

(22) Filed: Jan. 24, 2007

(65) Prior Publication Data
US 2007/0203468 A1 Aug. 30, 2007

(30) Foreign Application Priority Data
Feb. 28, 2006 (JP) ............................. 2006-054024
Mar. 3, 2006 (JP) ............................. 2006-058705

(51) Int. Cl.
*A61F 13/15* (2006.01)
(52) U.S. Cl. .............. 604/385.31; 604/378; 604/385.01
(58) Field of Classification Search ................. 604/378, 604/385.01, 385.31
See application file for complete search history.

(56) References Cited

U.S. PATENT DOCUMENTS

| | | | | |
|---|---|---|---|---|
| 4,578,071 A | * | 3/1986 | Buell | 604/379 |
| 5,019,066 A | * | 5/1991 | Freeland et al. | 604/385.27 |
| 6,280,426 B1 | * | 8/2001 | Turner et al. | 604/385.01 |
| 6,425,889 B1 | * | 7/2002 | Kitaoka et al. | 604/385.01 |
| 2005/0273073 A1 | * | 12/2005 | Suzuki et al. | 604/385.101 |

FOREIGN PATENT DOCUMENTS

JP 2004-358099 12/2004

* cited by examiner

*Primary Examiner*—Tatyana Zalukaeva
*Assistant Examiner*—Lynne Anderson
(74) *Attorney, Agent, or Firm*—Lowe Hauptman Ham & Berner, LLP

(57) ABSTRACT

A disposable diaper includes so that a sweat-absorbent sheet attached to the inner side of the diaper can maintain its sweat absorbing function during use of the diaper. The inner side of front or rear waist region constituting the disposable diaper is covered with a hydrophobic sheet and the sweat-absorbent sheet is bonded to the inner surface of the hydrophobic sheet. The hydrophobic sheet has a first sealing-free zone extending, inclusive of a first lower edge, in a circumferential direction so as to be left free from the inner side of the diaper and a first sealing zone extending above the first sealing-free zone and bonded to the inner side of the diaper. The sweat-absorbent sheet has a second lower edge extending in the circumferential direction above the first lower edge of the hydrophobic sheet, a second sealing-free zone extending, inclusive of the second lower edge, in the circumferential direction so as to be left free from the hydrophobic sheet and a second sealing zone extending above the second sealing-free zone and bonded to the hydrophobic sheet. A lower end of the first sealing zone is provided so as to lie below a lower end of the second sealing zone.

20 Claims, 6 Drawing Sheets

DISPOSABLE DIAPER

BACKGROUND OF THE INVENTION

The present invention relates to a disposable diaper and more particularly to such a diaper provided with a sweat-absorbent sheet.

Disposable diapers of which the inner side adapted to come in contact with the wearer's skin is partially defined by a sweat-absorbent sheet has already been well known. In the case of a diaper disclosed, for example, in Japanese Unexamined Patent Application Publication No. 2004-358099 (REFERENCE), a pair of end flaps respectively extend outward from longitudinally opposite ends of an absorbent assembly and respective inner surfaces of these end flaps are formed from water-repellent nonwoven fabric layers to which, in turn, sweat-absorbent sheets prepared separately of the water-repellent nonwoven fabric are bonded. As viewed in a vertical direction of the diaper put on the wearer's body, lower ends of the respective water-repellent nonwoven fabric layers overlap a liquid-pervious topsheet covering the absorbent assembly from the inner side.

The sweat-absorbent sheet used in the conventional disposable diaper is usually apt to come in close contact with the wearer's skin as the sweat-absorbent sheet is wetted with absorbed sweat. Consequentially, the sweat-absorbent sheet is apt to move together with the wearer's skin in the vertical direction as the wearer's skin moves relatively to the diaper. In addition, particularly in the case of the diaper as disclosed in REFERENCE, the water-repellent sheet to which the sweat-absorbent sheet is bonded is also apt to move in response to movement of the sweat-absorbent sheet. Depending on a manner in which the water-repellent sheet is bonded to the topsheet, the lower end of the water-repellent sheet may be folded upward with respect to the diaper and partially cover the lower end of the sweat-absorbent sheet. As a result, the surface area of the sweat-absorbent sheet expected to come in contact with the wearer's skin may be substantially reduced and it may be impossible for the sweat-absorbent sheet to exert the predetermined sweat absorbing ability.

SUMMARY OF THE INVENTION

In view of the problem as has been described above, it is an object of the present invention to improve the conventional diaper including the sweat-absorbent sheet so that a function required for the sweat-absorbent sheet can be maintained during use thereof.

According to the present invention, there is provided a disposable diaper comprising a crotch region, a front waist region extending forward from the crotch region and a rear waist region extending rearward from the crotch region wherein the front waist region and rear waist region respectively having a front edge and a rear edge cooperating together to define a peripheral edge of a waist-hole, a body fluid absorbent core extending in the crotch region and further into the front waist region and the rear waist region wherein the body fluid absorbent core has a front end in the front waist region and a rear end in the rear waist region, a liquid-pervious sheet extending on an inner side of the crotch region and a liquid-impervious sheet extending on an outer side of the crotch region so as to sandwich the body fluid absorbent core therebetween wherein on the inner side, hydrophobic sheets covering the front and rear waist regions in a zone defined between a vicinity of the front edge of the front waist region and a vicinity of the front end of the core rear edge, and between a vicinity of the rear edge of the rear waist region and a vicinity of the rear end of the core, and a sweat-absorbent sheet attached to a part of an inner surface of the hydrophobic sheet in any one of the front and rear waist regions.

The present invention further comprises: the hydrophobic sheet to which the sweat-absorbent sheet is attached has a vertical dimension larger than a vertical dimension of the sweat-absorbent sheet as viewed in a vertical direction of the diaper wherein the hydrophobic sheet has a first upper edge extending circumferentially of the diaper in the vicinity of the peripheral edge of the waist-hole, a first lower edge extending circumferentially of the diaper in the vicinity of any one of the front and rear ends of the core, a first sealing-free zone extending, inclusive of the first lower edge, circumferentially of the diaper so as to be left free from the liquid-pervious sheet and a first sealing zone extending above the first sealing-free zone so as to be bonded to the liquid-pervious sheet. The sweat-absorbent sheet has a second upper edge lying below the first upper edge of the hydrophobic sheet so as to extending circumferentially of the diaper, a second lower edge lying above the first lower edge of the hydrophobic sheet so as to extend, inclusive of the second lower edge, circumferentially of the diaper, a second sealing-free zone extending circumferentially of the diaper so as to be left free from the hydrophobic sheet and second sealing zone lying above the second sealing-free zone so as to be bonded to the hydrophobic sheet. A lower end of the first sealing section lies below a lower end of the second sealing zone.

According to one preferred embodiment of the present invention, the rear waist region is provided with a plurality of elastic members bonded thereto while stretched in circumferential direction so as to form gathers undulating in the circumferential direction and, in the sweat-absorbent sheet, the vertical dimension of the second sealing-free zone is in a range of 5 to 30 mm so that the second sealing-free zone may be formed with gathers each having a width larger than each of the gathers formed by the second sealing zone.

According to another preferred embodiment of the present invention, the sweat-absorbent sheet has a third sealing-free zone extending, inclusive of the second upper edge, in the circumferential direction so as to be left free from the hydrophobic sheet, the vertical dimension of the third sealing-free zone is in a range of 5 to 30 mm so that the third sealing-free zone may be formed with gathers each having a width larger than each of the gathers formed by the second sealing zone.

According to still another preferred embodiment of the present invention, the vertical dimension of the first sealing-free zone in the hydrophobic sheet is in a range of 2 to 20 mm and there is no possibility that the first sealing-free zone might overlap the sweat-absorbent sheet even when the first sealing-free zone is folded back toward the first upper edge.

In the disposable diaper according to the present invention, the sweat-absorbent sheet is attached to the inner surface of any one of the front and rear waist regions and the hydrophobic sheet has the first sealing-free zone extending, inclusive of the first lower edge, in the circumferential direction and the first sealing zone extending above the first sealing-free zone. The hydrophobic sheet is placed upon but left free from the liquid-pervious topsheet covering the body fluid absorbent core in the first sealing-free zone and bonded to the liquid-pervious topsheet in the first sealing zone. The second sealing zone in which the sweat-absorbent sheet is bonded to the hydrophobic sheet is defined above the first sealing-free zone and therefore, even if the first sealing-free zone of the hydrophobic sheet is curled upward with respect to the diaper, it is not apprehended that the sweat-absorbent sheet also might be turned upward and its function as the sweat-absorbent sheet might be deteriorated.

In the diaper according to the present invention, the second sealing-free zone or the third sealing-free zone of the sweat-absorbent sheet is formed with gathers having a pitch larger than a pitch of gathers formed in the second sealing zone. Thus, the second lower edge or the second upper edge of the sweat-absorbent sheet included in these gathers can easily reach the bottoms of the depressions formed, for example, along the spine of the diaper wearer and absorb sweat present therein.

In the diaper according to the present invention, it is not apprehended that the first sealing-free zone might overlap the sweat-absorbent sheet even if the first sealing-free zone of the hydrophobic sheet is folded back toward the first upper edge of the hydrophobic sheet. In other words, there is no anxiety that the sweat-absorbent sheet might be covered with the first sealing-free zone folded back in this manner. Consequentially, the sweat-absorbent sheet is able to maintain its proper function without apprehension that the effective surface area of the sweat-absorbent sheet might be substantially reduced.

DETAILED DESCRIPTION OF PREFERRED EMBODIMENTS

Details of the present invention will be more fully understood from the description of a pull-on disposable diaper as an embodiment of the invention given hereunder with reference to the accompanying drawings.

Figure 1:
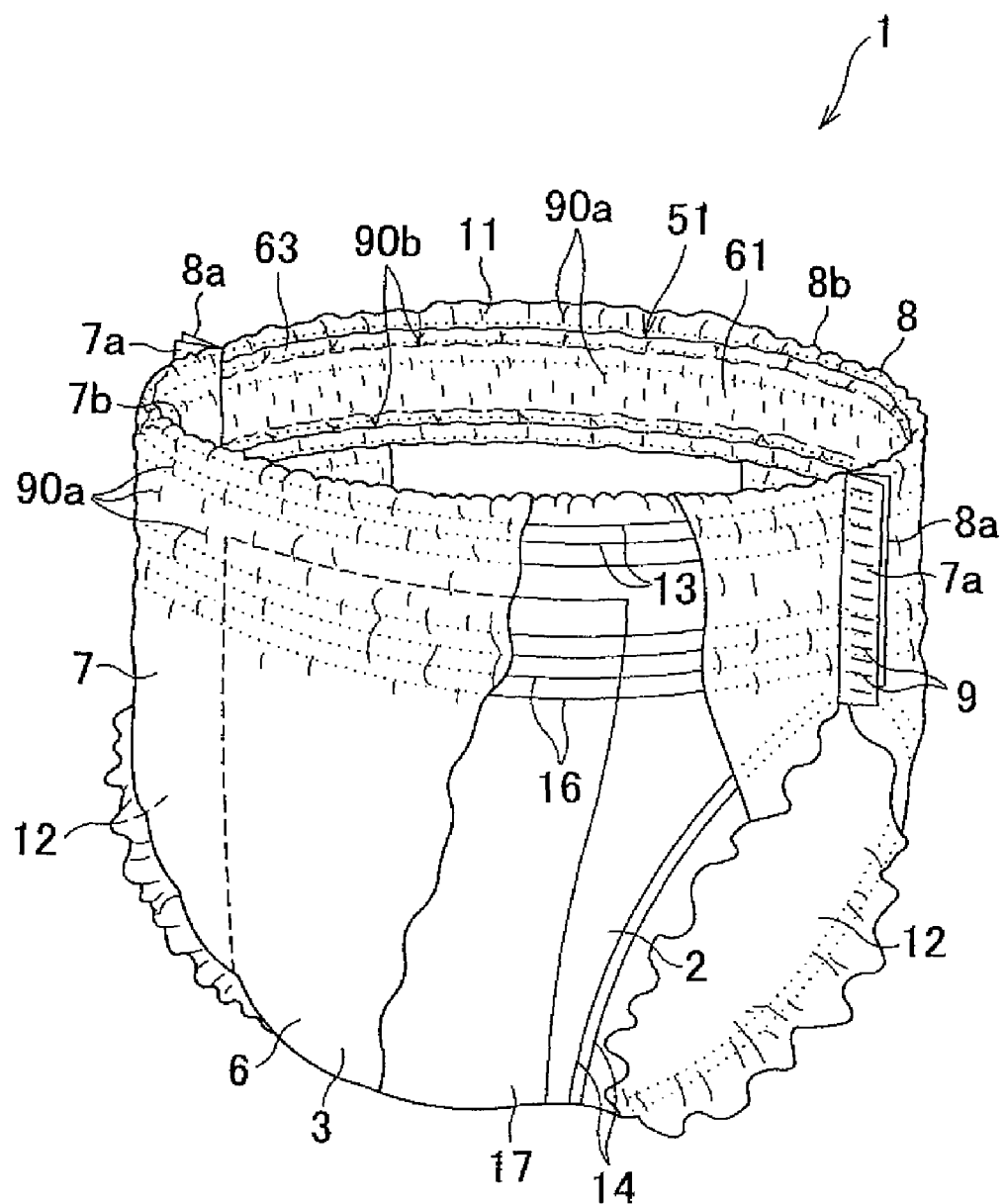
FIG. 1 is a partially cutaway perspective view showing a diaper according to the present invention.
Figure 1:
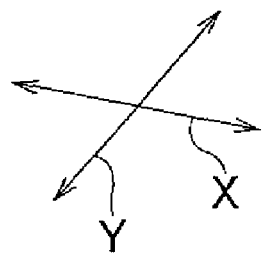

FIG. 1 is a partially cutaway perspective view showing a diaper 1 according to the present invention. The diaper 1 is of pull-on type and basically formed from a hydrophobic inner sheet 2 and a hydrophobic outer sheet 3 placed upon each other and bonded together by hot melt adhesives (not shown). The diaper 1 comprises a crotch region 6, a front waist region 7 extending forward from the crotch region 6 and a rear waist region 8 extending rearward from the crotch region 6 wherein transversely opposite side edges 7a, 7a and 8a, 8a of the front and rear waist regions 7, 8 are joined together at sealing zones 9 arranged intermittently in a vertical direction as viewed in FIG. 1 so as to define a waist-hole 11 and a pair of leg-holes 12. In a vicinity of a peripheral edge of the waist-hole 11, a plurality of waist-surrounding elastic members 13 are laid between the inner and outer sheets 2, 3 so as to extend in a circumferential direction and bonded in a stretched state to at least one of the inner and outer sheets 2, 3. In like wise, a plurality of leg-surrounding elastic members 14 are laid between the inner and outer sheets 2, 3 in a vicinity of peripheral edges of the respective leg-holes 12 so as to extend in a circumferential direction and bonded in a stretched state to at least one of the inner and outer sheets 2, 3. In addition to the elastic members as have been described above, a plurality of auxiliary elastic members 16 are laid between the inner and outer sheets 2, 3 in a region defined between front and rear halves 7b, 8b constituting the peripheral edge of the waist-hole 11, on one hand, and the peripheral edges of the respective leg-holes 12, on the other hand, so as to extend in a circumferential direction in parallel to the waist-surrounding elastic members 13 and bonded in a stretched state to at least one of the inner and outer sheets 2, 3. The diaper 1 further includes a liquid-impervious leak-barrier sheet 17 sandwiched between the inner and outer sheets 2, 3 extending in the crotch region 6 and further extending into the front and rear waist regions 7, 8.

Figure 2:
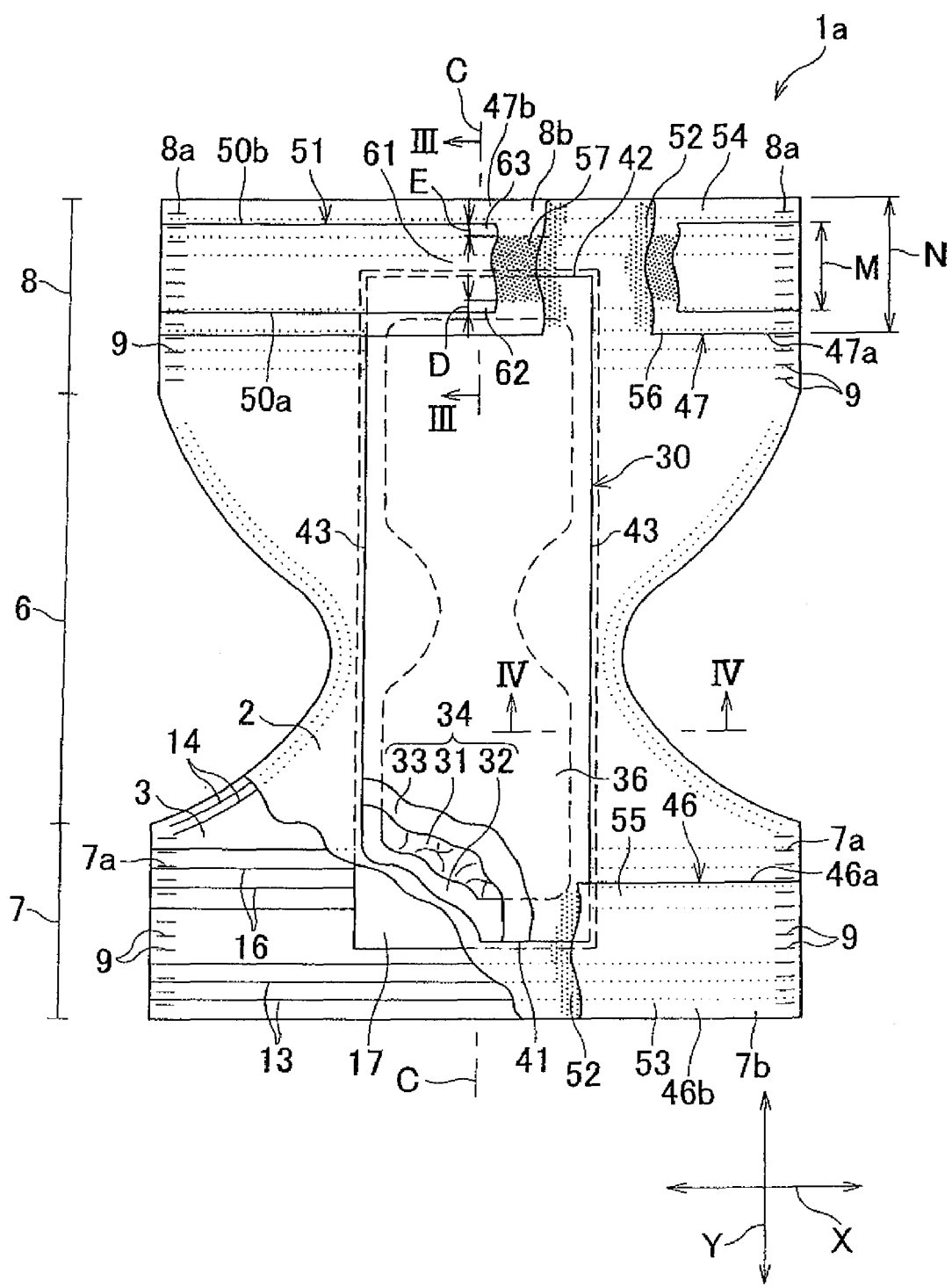
FIG. 2 is a partially cutaway plan view showing the diaper of FIG. 1 as disintegrated along transversely opposite sides thereof and then developed.

FIG. 2 is a partially cutaway plan view showing a diaper 1a corresponding to the diaper 1 of FIG. 1 with the front and rear waist regions 7, 8 disintegrated along the respective series of sealing zones 9 and the diaper 1 as a whole developed in a transverse direction indicated by a double-headed arrow X as well as in a back-and-forth direction indicated by a double-headed arrow Y. In FIG. 2, an inner side of the diaper 1a faces the viewer. The diaper 1a is provided in its transverse middle with a body fluid absorbent assembly 30. This body fluid absorbent assembly 30 comprises a liquid-absorbent material 31 such as fluff pulp fibers or a mixture of fluff pulp fibers and super-absorbent polymer particles wrapped with a tissue paper 32, 33 in a sandwich fashion to form a body fluid absorbent core 34 of which the inner side is covered with a liquid-pervious and hydrophilic topsheet 36 and the outer side is put to face the leak-barrier sheet 17. In this manner, the body fluid absorbent core 34 is sandwiched between the liquid-pervious sheet and the liquid-impervious sheet. In the illustrated embodiment, the inner sheet 2 is sandwiched between the core 34 and the leak-barrier sheet 17. The core 34 of such a construction has transversely opposite side edges 43 extending in the crotch region and further into the front and rear waist regions 7, 8, a front end 41 extending in the transverse direction and a rear end 42 extending also in the transverse direction. In the front and rear waist regions 7, 8, the front and rear halves 7b, 8b constituting the peripheral edge of the waist-hole 11 in FIG. 1 extend in the transverse direction X in FIG. 2. Referring to FIG. 2, the hourglass-shaped outer sheet 3 has front and rear turnbacks 46, 47 defined by portions of the outer sheet 3 folded back onto the inner side of the diaper 1 respectively along the front and rear halves 7b, 8b constituting the peripheral edge of the waist-hole 11. These turnbacks 46, 47 respectively correspond to the portions of the outer sheet 3 extending downward from the front and rear halves 7b, 8b constituting the peripheral edge of the waist-hole 11. Lower ends of these turnbacks 46, 47 respectively define front and rear lower edges 46a, 47b while the front and rear halves 7b, 8b respectively define front and rear upper edges 46b, 47b of these turnbacks 46, 47. The front turnback 46 covers the front end 41 of the core 34 and a vicinity thereof by the intermediary of the topsheet 36 while the rear turnback 47 covers the rear end 42 of the core 34 by the intermediary of the topsheet 36. The rear turnback 47 is provided on its inner side with a seat-absorbent sheet 51.

Referring again to FIG. 2, the front turnback 46 has a front sealing zone 53 in which the front turnback 46 is bonded to both the inner sheet 2 and the topsheet 36 by an adhesive 52 such as a hot melt adhesive (See FIG. 3 also) and a front sealing-free zone 55 extending, inclusive of the front lower edge 46a, in the transverse direction X. In the front sealing-free zone 55, the front turnback 46 is left free from both the inner sheet 2 and the topsheet 36. In a similar manner, the rear turnback 47 has a rear sealing zone 54 in which the rear turnback 47 is bonded to both the inner sheet 2 and the topsheet 36 by means of adhesive 52 and a rear sealing-free zone 56, extending, inclusive of the rear lower edge 47a, in the transverse direction X. In the rear sealing-free zone 56, the rear turnback 47 is left free from both the inner sheet 2 and the topsheet 36. Each of the preferred front and rear sealing-free zones 55, 56 has a vertical dimension in a range of 2 to 20 mm as viewed in the diaper 1 of FIG. 1. In the illustrated embodiment, the front turnback 46 and the rear turnback 47 are formed by the hydrophobic outer sheet 3 which advantageously eliminates a problem possibly occurring in the front and rear waist regions 7, 8 such that body fluids once absorbed by the body fluid absorbent assembly 30 might exude from the body fluid absorbent assembly 30 and come in contact with the wearer's skin.

The sweat absorbent sheet 51 extends in the transverse direction X beyond the side edges 43 of the body fluid absorbent assembly 30 and, in the embodiment illustrated by FIG. 2, extends to the side edges 8a of the inner sheet 2. The sweat-absorbent sheet 51 has a lower edge 50a and an upper edge 50b both extending substantially in parallel to the rear lower edge 47a of the rear turnback 47. A dimension M between these lower edge 50a and upper edge 50b is smaller than a vertical dimension N of the rear turnback 47, i.e., the dimension N between the rear lower edge 47a and the rear upper edge 47b. Such sweat-absorbent sheet 51 has a sealing zone 61 in which the sweat-absorbent sheet 51 is bonded to the inner surface of the rear turnback 47, i.e., the surface of the rear turnback 47 facing the diaper wearer's skin by means of adhesive 57 such as hot melt adhesive (See FIG. 3 also) applied, for example, in the form of small dots distributed at a density in a range of 1 to 20 dots/cm$^2$. This sealing zone 61 is disposed in the middle of the sweat-absorbent sheet 51 as viewed in the vertical direction of the diaper 1. The sweat-absorbent sheet 51 additionally has a lower sealing-free zone 62 defined by a dimension D from the lower edge 50a to the sealing zone 61, inclusive of the lower edge 50a, in which the sweat-absorbent sheet 51 is left free from the rear turnback 47 and an upper sealing-free zone 63 defined by a dimension E from the upper edge 50b to the sealing zone 61, inclusive of the upper edge 50b, in which the sweat-absorbent sheet 51 is left free from the rear turnback 47.

Figure 3:
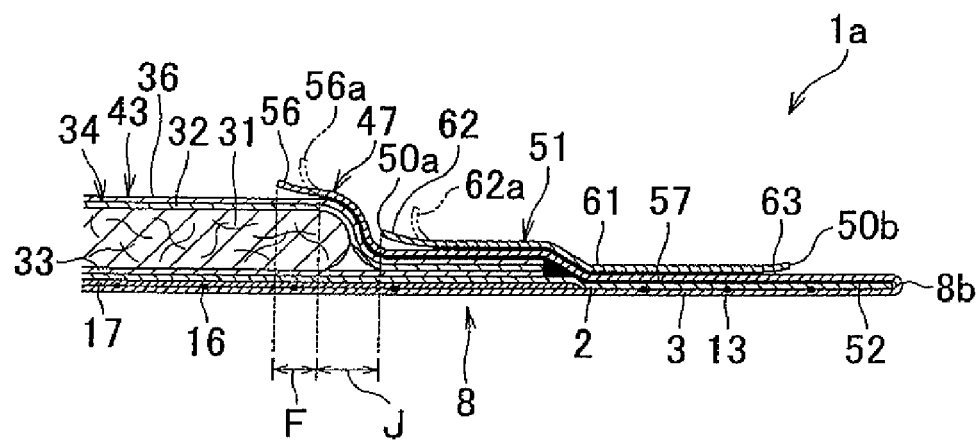
FIG. 3 is a sectional view taken along the line III-III in FIG. 2.

FIG. 3 is a sectional view taken along the line III-III in FIG. 2. As will be apparent from FIGS. 2 and 3, the lower sealing-free zone 62 in the sweat-absorbent sheet 51 is located aside from the rear sealing-free zone 56 in the rear turnback 47 to the right side. In other words, the diaper 1 of FIG. 1 has the lower sealing-free zone 62 formed above the rear sealing-free zone 56. Such arrangement ensures that, even if the rear sealing-free zone 56 of the rear turnback 47 is curled up or partially peeled off as indicated by imaginary line 56a during use of the diaper 1, the sweat-absorbent sheet 51 will not be affected thereby to be curled up or partially peeled off. It is also ensured that, even if the lower sealing-free zone 62 of the sweat-absorbent sheet 51 is curled up or partially peeled off as indicated by imaginary line 62a, the rear turnback 47 will not be affected thereby to be curled up or partially peeled off. The lower sealing-free zone 62 and the rear sealing-free zone 56 arranged as has been described above are preferred to those arranged in a manner that the sealing zone 61 extends downward beyond the rear sealing zone 54 in the vertical direction of the rear waist region 8 and the lower sealing-free zone 62 of the sweat-absorbent sheet 51 may move upward together with the wearer's skin relatively to the diaper 1 when the sweat-absorbent sheet 51 is wetted with sweat so as to stick fast to the wearer's skin. Such upward movement of the lower sealing-free zone 62 results in that the rear sealing-free zone 56 of the rear turnback 47 may be curled up together with the sweat-absorbent sheet 51 and the rear turnback 47 may be subjected, in the rear sealing zone 54, to a peeling force sufficiently to peel the rear turnback 47 off from the topsheet 36. Generation of such peeling force can be reliably avoided by the rear turnback 47 and the sweat-absorbent sheet 51 of the arrangement shown in FIG. 2.

In the preferred embodiment shown in FIG. 3, the rear sealing-free zone 56 is uniquely dimensioned to ensure that the rear turnback 47 of the rear waist region 8 will not cover the sweat-absorbent sheet 51 more or less even if the rear sealing-free zone 56 is curled up as indicated by the imaginary line 56a. This is achieved by setting a dimension F of the rear sealing-free zone 56, i.e., a dimension F measured from the rear lower edge 47a of the rear turnback 47 to the lower edge of the rear sealing zone 54 smaller than a dimension J measured from the lower end of the rear sealing zone 54 to the lower edge 50a of the sweat-absorbent sheet 51. Depending on whether the diaper 1 is for infant or for adult, the dimension F of the rear sealing-free zone 56 of the rear turnback 47 is preferably in a range of 2 to 20 mm. The rear sealing-free zone 56 dimensioned in this manner allows the rear lower edge 47a to come in soft contact with the wearer's skin. The lower sealing-free zone 62 and the upper sealing-free zone 63 of the sweat-absorbent sheet 51 preferably have vertical dimensions D, E preferably in a range of 2 to 30 mm, and more preferably in a range of 5 to 30 mm. Contraction of the waist-surrounding elastic members 13 and the auxiliary waist-surrounding elastic members 16 causes the front and rear waist regions 7, 8 to be formed with fine gathers 90a which circumferentially undulate. Simultaneously, the sealing zone 61 of the sweat-absorbent sheet 51 lying in the rear waist region 8 also is formed with such fine gathers 90a (See FIG. 1). However, contraction of these elastic members 13, 16 does not directly affect the lower sealing-free zone 62 and the upper sealing-free zone 63 both left free from the inner side of the rear waist region 8. Consequentially, these sealing-free zones 62, 63 are formed with gathers 90b being sufficiently larger and higher than each of the gathers 90a (See FIG. 1) to reach bottoms of depressions formed along the spine of the diaper wearer and thereby to absorb sweat exuding therein which can not be absorbed by the fine gathers 90a). In the sweat-absorbent sheet 51, the dimension D of the lower sealing-free zone 62 and the dimension E of the upper sealing-free zone 63 may be set to be equal to or different from each other.

Referring again to FIG. 3, sheets of tissue paper 32, 33 extending rightward from a right end (corresponding to an upper end as viewed in FIG. 2) of the liquid-absorbent material 31 constituting the body fluid absorbent assembly 30 are placed upon and bonded to the topsheet 36 by means of hot melt adhesive (not shown). The sheet of tissue paper 33 is bonded also to the inner sheet 2.

Figure 4:
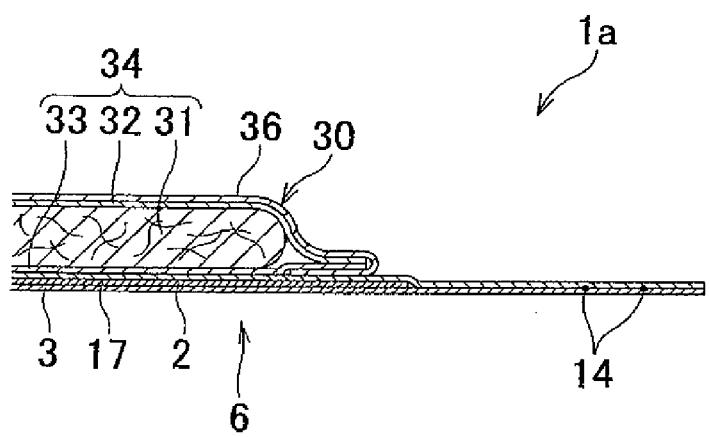
FIG. 4 is a sectional view taken along the line IV-IV in FIG. 2.

FIG. 4 is a sectional view taken along the line IV-IV in FIG. 2. In the crotch region 6 of the diaper 1a, the inner sheet 2, the outer sheet 3 and the leak-proof sheet 17 sandwiched between these inner and outer sheets 2, 3 are placed upon and bonded to one another by hot melt adhesive (not shown). The leg-surrounding elastic members 14 are sandwiched between the inner and outer sheets 2, 3 so as to extend along the transversely opposite side edges of these inner and outer sheets 2, 3. In the body fluid absorbent assembly 30, the inner surface, the side surfaces and a part of the outer surface of the core 34 are covered with the topsheet 36 which is bonded to the sheets of tissue paper 32, 33 by hot melt adhesives (not shown).

In the diaper 1 constructed in the manner as has been described above, the inner sheet 2 as well as the outer sheet 3 may be formed from a hydrophobic sheet material such as a nonwoven fabric made of thermoplastic synthetic fibers or a film made of thermoplastic synthetic resin. The leak-barrier sheet 17 may be formed from a liquid-impervious sheet such as a film made of thermoplastic synthetic resin. The topsheet 36 may be formed from a liquid-pervious sheet material such as a nonwoven fabric made of thermoplastic synthetic resin or an aperture film made of thermoplastic synthetic resin, modified to become hydrophilic, if necessary. While any material of well known art or prior art may be used as stock materials for the sweat-absorbent sheet 51, the sweat-absorbent sheet 51 exemplarily shown in FIG. 5 is preferable to obtain the diaper 1 providing refreshing feeling.

Figure 5:
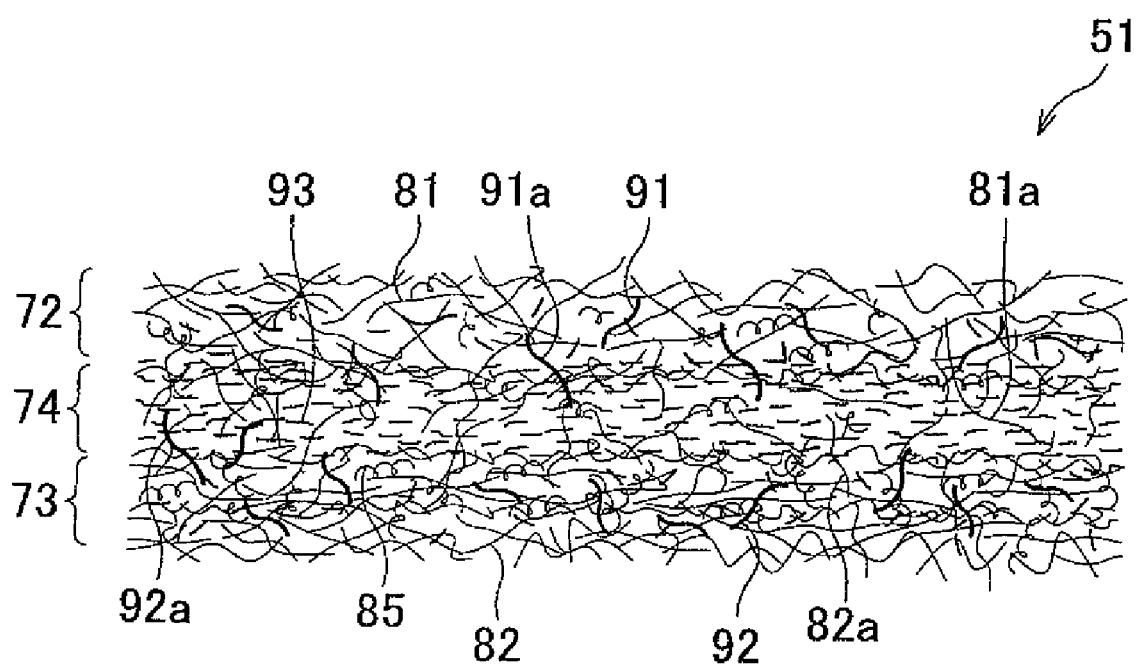
FIG. 5 is a sectional view illustrating an example of sweat-absorbent sheet.

FIG. 5 is a sectional view showing the sweat-absorbent sheet 51 which is suitable for the present invention. The sweat-absorbent sheet 51 comprises an upper layer 72, a lower layer 73 and an intermediate layer 74 interposed between these two layers 72, 73. The upper and lower layers 72, 73 principally comprise first and second hydrophobic fibers 81, 82 both made of thermoplastic synthetic resin mixed with a relatively small amount of first and second hydrophilic fibers 91, 92. The intermediate layer 74 principally comprises third hydrophilic fibers 93 and sometimes the first and second hydrophobic fibers 81, 82 as well as the first and second hydrophilic fibers 91, 92 extend into the intermediate layer 74. The first and second hydrophobic fibers extending into the intermediate layer 74 are designated by reference numerals 81a, 82a, respectively, and the first and second hydrophilic fibers extending into the intermediate layer 74 are designated by reference numerals 91a, 92a, respectively. In these upper, lower and intermediate layers 72, 73, 74, respectively, as well as between each pair of the adjacent layers thereof, crimped hydrophobic composite fibers 85 is present. These fibers 81, 82, 91, 92, 93 constituting the sweat-absorbent sheet 51 are not only mechanically interlaced one with another but also bonded together in most of regions in which these fibers are kept in contact with the composite fibers 85 as the composite fibers 85 is fused. It should be appreciated that a fineness of the hydrophilic fibers is illustrated to be higher than a fineness of the hydrophobic fibers in order to discriminate the hydrophilic fibers from the hydrophobic fibers.

The first, second and third hydrophilic fibers 91, 92, 93 are coated with medical ingredient (not shown) providing antibacterial effect or bactericidal effect. While such medical ingredient sometimes clings to the first and second hydrophobic fibers 81, 82, most of the medical ingredient clings to the first, second and third hydrophilic fibers 91, 92, 93 in the preferred sweat-absorbent sheet 51.

On the assumption that the upper layer 72 of such sweat-absorbent sheet 51 is put in contact with the wearer's skin, the first hydrophilic fibers 91 constituting the upper layer 72 functions to absorb an amount of sweat being present over the contact area. The amount of sweat absorbed in this manner percolates and spreads toward the intermediate layer 74 and is then retained by the third hydrophilic fibers 93 constituting the intermediate layer 74. The amount of sweat thus retained is prevented by the presence of the first hydrophobic fibers 81 constituting the intermediate layer 72 from flowing back and coming in contact with the wearer's skin. Consequentially, the diaper wearer is free from feeling of wetness due to sweat and experiences refreshing feeling. The third hydrophilic fibers 93 serving to retain the amount of sweat is coated with the medical ingredient as has been described above and therefore proliferation of undesirable bacteria such as *Staphylococcus epidermidis* is constricted and thereby eruption of heat rash possibly caused by such bacterial is constricted. Such medical ingredient may be selected from a group of quaternary ammonium salts such as alkylpyridinium salt, alkylbenzyldimethylammonium salt, alkyltrimethylammonium salt (benzalkonium chloride), dialkyldimethylammonium salt and benzetonium chloride. The medical ingredient may be used in form of a mixture with another ingredient such as catechin.

The first hydrophobic fiber 81 constituting the upper layer 72 of the sweat-absorbent sheet 51 is made of thermoplastic synthetic resin such as polyester, polypropylene or nylon preferably having a melting point higher than that of polyethylene, fiber length at least of 30 mm and fineness in a range of 0.1 to 5 dtex. The first hydrophilic fibers 91 constituting the upper layer 72 is made of hydrophilic fibers such as rayon, cotton or pulp preferably having fiber length at least of 30 mm. The second hydrophobic fibers 82 and the second hydrophilic fibers 92 constituting the lower layer 73 may be made of the same materials as the corresponding fibers used in the upper layer 72, although it is not essential to form the upper and lower layers 72, 73 as has been described just above. The third hydrophilic fiber 93 constituting the intermediate layer 74 is made of hydrophilic fibers such as rayon, cotton or pulp. There is no apprehension that the fibers constituting the intermediate layer 74 might be exposed on the surfaces of the sweat-absorbent sheet 51 even if pulp fibers having fiber length of 5 mm or less is used as the third hydrophilic fibers 93. It is for the reason that the intermediate layer 74 is sandwiched between the upper and lower layers 72, 73. Therefore, pulp fiber available at unit price lower than unit cost at which rayon fibers is available can be used to reduce a manufacturing cost for the sweat-absorbent sheet 51. The crimped composite fibers 85 contained in the respective layers of the sweat-absorbent sheet 51 may be, for example, composite fibers consisting of polyethylene as its sheath component and polypropylene as its core component of an amount corresponding to 5 to 20% by weight of the sweat-absorbent sheet 51 as a whole. The composite fiber 85 functions to maintain the shape of the sweat-absorbent sheet 51 constant before as well as after occurrence of sweat-absorption since polyethylene as the sheath component is fusion-bonded to the first hydrophobic fibers 81 and the second hydrophobic fibers 82 with which the sheath component is placed in contact. More specifically, until the sweat-absorbent sheet 51 actually absorbs sweat after it has been manufactured, the composite fibers 85 serves to prevent the sheet 51 from getting out of its initial texture and/or from fluffing. In the sweat-absorbent sheet 51 having absorbed sweat, although the first, second and third hydrophilic fibers 91, 92, 93 tend to have respective apparent volumes swollen due to sweat absorption, the composite fiber 85 serves to maintain the shape of the sweat-absorbent sheet 51 substantially constant and prevent the sweat-absorbent sheet 51 from getting out of its initial texture which would lead to an undesirable situation in which the third hydrophilic fiber 93 wetted with sweat may come in contact with the wearer's skin.

The inventors measured amount of perspiration in lumbar region on three infants who were two years old. Measurement was carried out with the conventional diapers put on these infants for three hours in a room at a temperature of $33 \pm 1°$ C. and RH of $75 \pm 5\%$ using a sudorometer SKD-1000 manufactured by SKINOS CO., LTD. (Nagoya City, Aichi Prefecture) and an average amount of perspiration per unit skin surface area (1 $m^2$) of 192 g/hr was obtained. The diaper usually remains put on two to three years old infant for about three hours and, in view of this, the sweat-absorbent sheet 51 preferably has a sweat-absorbing capacity at least three times the average amount of perspiration per hour, i.e., in a range of about 550 $g/m^2$ to about 570 $g/m^2$. The inventors made an example of the sweat-absorbent sheet 51 wherein the component fibers thereof illustrated in FIG. 5 were selected in a manner as follows. Polyester fibers having a basis weight of 8.4 g/m² as the first hydrophobic fibers 81, polyester fibers having a basis weight of 4.9 g/m² as the second hydrophobic fiber 82, rayon fibers having a basis weight of 3.6 g/m² as the first hydrophilic fibers 91, rayon fibers having a basis weight of 4.9 g/m² as the second hydrophilic fibers 92, pulp fibers having a basis weight of 12 g/m² as the third hydrophilic fibers 93 and composite fibers consisting of polypropylene forming the core component and polyethylene forming the sheath as the composite fiber 85 were used to obtain web having a basis weight of 38 g/m² which was, in turn, coated with a mixture of cetylpiridinium chloride and catechin to obtain a sweat-absorbent sheet 51 having a thickness of 0.5 mm. The sweat-absorbent sheet 51 obtained in this manner was dried for 5 minutes after immersed in water for three minutes and an then amount of water absorption was determined to be approximately 705 g/m². This means that, even if a time period for which the diaper is continuously put on the wearer's body exceeds three hours, a sufficient amount of sweat absorption per unit surface area (1 m²) of the wearer's skin can be ensured. This sweat-absorbent sheet 51 was cut into a size of about 55×285 mm and then attached to the diaper 1 for infant. This diaper 1 was put on a two years old infant for three hours and no sweat was observed in a region of the infant's skin in which the sweat-absorbent sheet 51 had been kept in contact with the wearer's skin.

Figure 6:
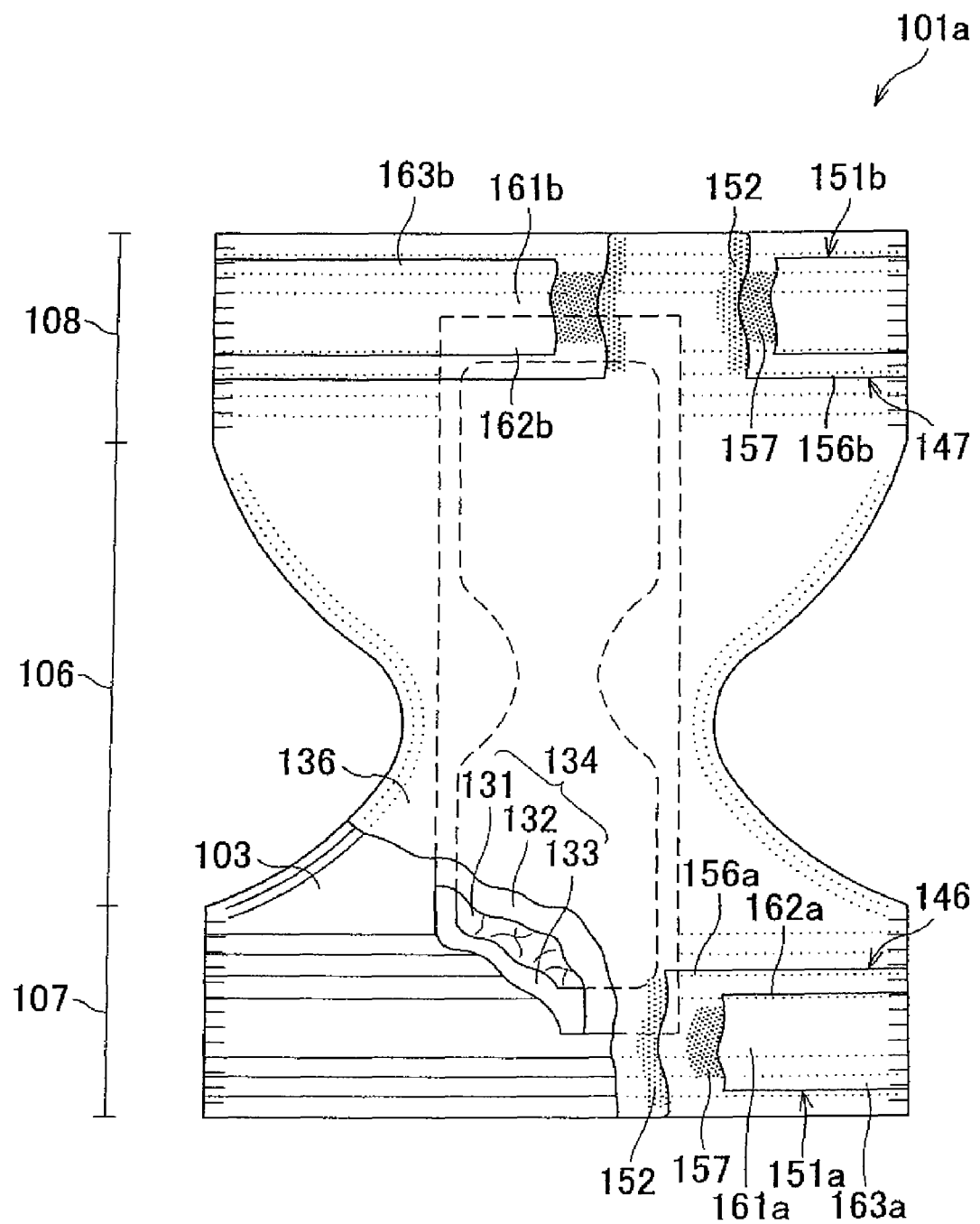
FIG. 6 is a view similar to FIG. 2, illustrating one preferred embodiment of the invention.

FIG. 6 is a view similar to FIG. 2, showing one preferred embodiment of the present invention wherein the respective regions or zones corresponding to those in FIG. 2 are designated by reference numerals which are the reference numerals plus 100. In a diaper 101a of FIG. 6, a core 134 comprising liquid-absorbent material 131 covered with sheets of tissue paper 132, 133 is sandwiched between an hourglass-shaped liquid-pervious topsheet 136 and a liquid-impervious outer sheet 103. In a front waist region 107 and a rear waist region 108, the front turnback 46 and the rear turnback 47 both of hydrophobic nature are replaced by a hydrophobic front and rear sheets 146, 147, respectively, which are prepared separately of an outer sheet and bonded to the topsheet 136 by a hot melt adhesive 152. A front sweat-absorbent sheet 151a and a rear sweat-absorbent sheet 151b are bonded to these front and rear sheets 146, 147 by a hot melt adhesive 157. The front sweat-absorbent sheet 151a and the rear sweat-absorbent sheet 151b have front and rear sealing zones 161a, 161b, lower sealing-free zones 162a, 162b and upper sealing-free zones 163a, 163b with respect to the front and rear hydrophobic sheets 146, 147, respectively. The front and rear sealing zones 161a, 161b are provided so as to be located above the front and rear sealing-free zones 156a, 156b in the front and rear hydrophobic sheets 146, 147, respectively, as the front and rear waist zones are connected with each other to obtain the hourglass-shaped diaper 101a. In the diaper 101a of FIG. 6, the front and rear hydrophobic sheets 146, 147 in the front and rear waist regions 107, 108 respectively function in the same manner as the front and rear turnbacks 46, 47 in the diaper 1 of FIG. 1.

Figure 7:
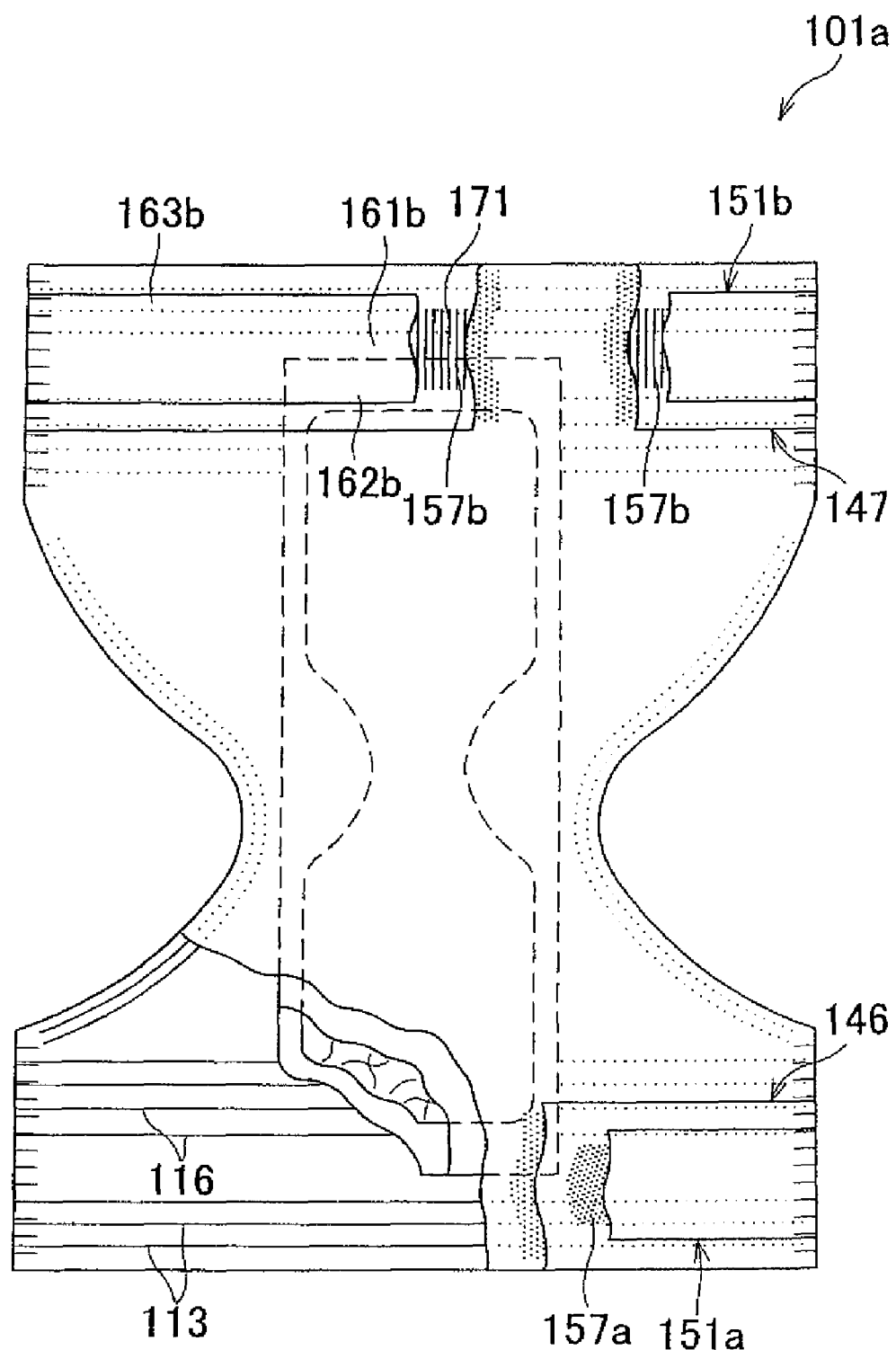
FIG. 7 is a view similar to FIG. 6, illustrating another preferred embodiment of the invention.

FIG. 7 is a view similar to FIG. 6, showing another preferred embodiment of the present invention. In the diaper 101a of FIG. 7, the rear sweat-absorbent sheet 151b is bonded to the rear hydrophobic sheet 147 by a hot melt adhesive 157b applied in a pattern of plural stripes 171 extending in parallel one to another. Each of these stripes 171 has a width in a range of 0.5 to 10 mm and each pair of the adjacent stripes 171 are preferably spaced from each other by 2 to 20 mm and more preferably in a range of 5 to 10 mm. The rear sweat-absorbent sheet 151b comprises the rear sealing zone 161b formed by a plurality of the stripes 171, the upper sealing-free zone 162a extending above a plurality of the stripes 171 and the lower sealing-free zone 162b extending just below a plurality of the stripes 171. In this diaper 101a, upon contraction of waist-surrounding elastic members 113 and waist-surrounding auxiliary elastic members 116 in the rear waist region 108, the sweat-absorbent sheet 151b is formed between each pair of the adjacent stripes 171 with a gather which semicylindrically protruding toward the inner side of the diaper 101a. With such sweat-absorbent sheet 151b, not only gathers formed in the upper sealing-free zone 162a and the lower sealing-free zone 162b but also gathers formed in the rear sealing zone 161b can easily reach bottoms of the depressions which are usually present along the spine of the diaper wearer. The gathers semicylindrically protruding define also air passages which vertically extend between the diaper 101a and the wearer's skin. It should be understood here that, in the diaper 101a of FIG. 7, the front sweat-absorbent sheet 151a is bonded to the front sheet 146 by means of hot melt adhesive 157a applied in a pattern of plural dots similar to the case shown by FIG. 6.

While the present invention has been described on the basis of the pants-type diaper disintegrated along the transversely opposite side edges thereof and then developed to be flattened, the invention is applicable also to the open-type diaper. Furthermore, the sweat-absorbent sheet may be selectively attached to the front waist region and/or the rear waist region without departing from the spirit and the scope of the invention.

The present invention makes it to manufacture a disposable diaper free from an anxiety that an effective surface area of the sweat-absorbent sheet might be substantially reduced during use of the diaper.

The entire discloses of Japanese Patent Application Nos. 2006-54024 filed on Feb. 28, 2006 and 2006-58705 filed on Mar. 3, 2006, respectively, including specification, drawings and abstract are herein incorporated by reference in their entirety.

What is claimed is:

1. A disposable diaper comprising:
   a crotch region,
   a front waist region extending forward from said crotch region and a rear waist region extending rearward from said crotch region, said front waist region and rear waist region respectively having a front edge and a rear edge cooperating together to define a peripheral edge of a waist-hole,
   a body fluid absorbent core extending in said crotch region and further into said front waist region and said rear waist region, said body fluid absorbent core having a front end in said front waist region and a rear end in said rear waist region,
   a liquid-pervious sheet extending on an inner side of said crotch region adapted to face a wearer's skin in use and a liquid-impervious sheet extending on an outer side of said crotch region adapted to face away from the wearer' skin in use so as to sandwich said body fluid absorbent core therebetween,
   on said inner side, hydrophobic sheets covering said front and rear waist regions in a zone defined between a vicinity of said front edge of said front waist region and a vicinity of said front end of said core, and between a vicinity of said rear edge of said rear waist region and a vicinity of said rear end of said core, each said hydrophobic sheet having
      an inner surface adapted to face the wearer's skin in use, and an outer surface opposite the inner surface, facing the liquid-pervious sheet and adapted to face away from the wearer's skin in use, a sweat-absorbent sheet which is directly attached to said inner surface of said hydrophobic sheet in said rear waist region and is adapted to contact the wearer's skin in use, and a plurality of elastic members directly bonded while stretched to the rear waist region so as to form gathers undulating circumferentially of said diaper in said sweat-absorbent sheet, wherein said hydrophobic sheet, to which said sweat-absorbent sheet is attached, has a vertical dimension larger than a vertical dimension of said sweat-absorbent sheet as viewed in a vertical direction of said diaper, and further comprises:

a first upper edge extending circumferentially of said diaper in the vicinity of the peripheral edge of said waist-hole;

a first lower edge extending circumferentially of said diaper in the vicinity of said rear end of said core;

a first sealing-free zone inclusive of said first lower edge, extending circumferentially of said diaper and free of direct attachment to said liquid-pervious sheet; and a first sealing zone extending above said first sealing-free zone and bonded to said liquid-pervious sheet, said sweat-absorbent sheet further comprises:

a second upper edge lying below said first upper edge of said hydrophobic sheet and extending circumferentially of said diaper;

a second lower edge lying above said first lower edge of said hydrophobic sheet and extending circumferentially of said diaper;

a second sealing-free zone inclusive of said second lower edge, extending circumferentially of said diaper and free of direct attachment to said hydrophobic sheet;

a third sealing-free zone inclusive of said second upper edge, extending circumferentially of said diaper and free of direct attachment to said hydrophobic sheet; and a second sealing zone lying above said second sealing-free zone and bonded to said hydrophobic sheet; and a lower end of said first sealing zone lying is below a lower end of said second sealing zone.

2. The disposable diaper defined by claim 1, wherein in said sweat-absorbent sheet, a vertical dimension in the vertical direction of said second sealing-free zone is in a range of 5 to 30 mm, said gathers comprise first gathers in said second sealing zone and second gathers in said second sealing-free zone, and each of said second gathers has a width larger than each of said first gathers.

3. The disposable diaper defined by claim 2, wherein a vertical dimension in the vertical direction of said third sealing-free zone is in a range of 5 to 30 mm, said third sealing-free zone is formed with said second gathers.

4. The disposable diaper defined by claim 1, wherein a vertical dimension in the vertical direction of said first sealing-free zone in said hydrophobic sheet is in a range of 2 to 20 mm and there is no possibility that said first sealing-free zone might overlap said sweat-absorbent sheet even when said first sealing-free zone is folded back toward said first upper edge.

5. The disposable diaper defined by claim 1, wherein said second sealing zone of said sweat-absorbent sheet is formed with first gathers, and said second and third sealing-free zones of said sweat-absorbent sheet are formed with second gathers, each of said second gathers is wider and higher than each of said first gathers thereby to absorb sweat which cannot be absorbed by said first gathers.

6. The disposable diaper defined by claim 2, wherein said sweat-absorbent sheet extends circumferentially of said diaper and overlays said elastic members in said rear waist region.

7. The disposable diaper defined by claim 1, wherein the second sealing zone of said sweat-absorbent sheet is bonded to the hydrophobic sheet by adhesive.

8. The disposable diaper defined by claim 7, wherein said adhesive is applied in a pattern of plural longitudinal stripes extending circumferentially of said diaper along the sweat-absorbent sheet.

9. The disposable diaper defined by claim 1, wherein said sweat-absorbent sheet comprises rear and front sweat-absorbent sheets attached to said outer surface of the respective hydrophobic sheets and extending circumferentially of said diaper along said rear and front waist regions, respectively.

10. The disposable diaper defined by claim 1, wherein said sweat-absorbent sheet comprises an inner layer having first hydrophilic and hydrophobic fibers and adapted to contact with the wearer's skin;

an outer layer having second hydrophilic and hydrophobic fibers; and an intermediate layer interposed between said inner and outer layers and has third hydrophilic fibers, wherein said layers of the sweat-absorbent sheet further comprise composite fibers, respectively, as well as between each pair of said adjacent layers thereof, said first and second hydrophobic fibers as well as the first and second hydrophilic fibers extend into the intermediate layer, and said first hydrophilic and hydrophobic fibers, second hydrophilic and hydrophobic fibers and third hydrophilic fibers of the sweat-absorbent sheet are bonded together in regions in which said first hydrophilic and hydrophobic fibers, second hydrophilic and hydrophobic fibers and third hydrophilic fibers contact with said composite fibers.

11. The disposable diaper defined by claim 10, wherein said first, second and third hydrophilic fibers are coated with medical ingredient providing antibacterial effect or bactericidal effect.

12. The disposable diaper defined by claim 1, wherein the hydrophobic sheet is sandwiched between (a) the sweat-absorbent sheet directly bonded to said hydrophobic sheet and (b) the liquid-pervious sheet underlying said hydrophobic sheet.

13. The disposable diaper defined by claim 2, wherein the second sealing-free zone and the third sealing-free zone are formed with the second gathers, and the second lower edge and the second upper edge of the sweat-absorbent sheet are included in the second gathers for absorbing sweat that not absorbed by the first gathers.

14. The disposable diaper defined by claim 1, wherein said first sealing zone extends continuously in the vertical direction across the rear end of the absorbent core and overlies the rear end of the absorbent core.

15. The disposable diaper defined by claim 14, wherein a vertical dimension in the vertical direction of the first sealing-free zone is less than that of the first sealing zone.

16. The disposable diaper defined by claim 15, wherein the vertical dimension of the first sealing-free zone is greater than that of the sweat absorbent-sheet.

17. The disposable diaper defined by claim 16, wherein
in said sweat-absorbent sheet, the vertical dimension of said second sealing-free zone is in a range of 5 to 30 mm and the vertical dimension of said third sealing-free zone is in a range of 5 to 30 mm, and
the vertical dimension of the second sealing zone is greater than those of the second and third sealing-free zones.

18. The disposable diaper defined by claim 15, wherein the vertical dimension of the second sealing zone is greater than those of the second and third sealing-free zones.

19. The disposable diaper defined by claim 18, wherein in said sweat-absorbent sheet, the vertical dimension of said second sealing-free zone is in a range of 5 to 30 mm and the vertical dimension of said third sealing-free zone is in a range of 5 to 30 mm.

20. The disposable diaper defined by claim 1, wherein a vertical dimension in the vertical direction of the second sealing zone is greater than those of the second and third sealing-free zones.

* * * * *